United States Patent
Kiedrowski

(10) Patent No.: US 11,206,974 B2
(45) Date of Patent: Dec. 28, 2021

(54) SURGICAL INSTRUMENT AND METHOD FOR PRODUCING A SURGICAL INSTRUMENT

(71) Applicant: OLYMPUS WINTER & IBE GMBH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 791 days.

(21) Appl. No.: 16/047,051

(22) Filed: Jul. 27, 2018

(65) Prior Publication Data
US 2018/0368674 A1    Dec. 27, 2018

Related U.S. Application Data

(63) Continuation of application No. PCT/EP2017/052556, filed on Feb. 6, 2017.

(30) Foreign Application Priority Data

Feb. 9, 2016   (DE) .................. 102016201905.8

(51) Int. Cl.
*A61B 1/00*     (2006.01)
*A61B 1/018*    (2006.01)
(Continued)

(52) U.S. Cl.
CPC ............ *A61B 1/307* (2013.01); *A61B 1/0008* (2013.01); *A61B 1/0011* (2013.01);
(Continued)

(58) Field of Classification Search
CPC . A61B 1/00066; A61B 1/00121; A61B 1/018; A61B 1/00119; A61B 1/00128
See application file for complete search history.

(56) References Cited

U.S. PATENT DOCUMENTS 4,967,732 A * 11/1990 Inoue .................. A61B 1/00137
                                                        600/139
5,735,793 A *  4/1998 Takahashi .......... A61B 1/00059
                                                        600/104
(Continued)

FOREIGN PATENT DOCUMENTS

DE        3206381 A1    9/1983
DE       19713275 A1   10/1998
(Continued)

OTHER PUBLICATIONS

International Search Report dated Apr. 18, 2017 issued in PCT/EP2017/052556.
(Continued)

*Primary Examiner* — Matthew J Kasztejna
(74) *Attorney, Agent, or Firm* — Scully, Scott, Murphy & Presser, P.C.

(57) ABSTRACT

A surgical instrument including: a main body; an elongated shaft tube connected to the main body, the shaft tube having at least one working channel tube arranged in an interior of the shaft tube, the at least one working channel tube extending in a longitudinal direction of the shaft tube; and a connection body coupled to a proximal end region of the main body; wherein a proximal end region of the at least one working channel tube is accommodated inside the connection body and is sealed with respect to the connection body.

8 Claims, 3 Drawing Sheets

(51) Int. Cl.
   *A61B 1/307*       (2006.01)
   *A61B 1/07*        (2006.01)
(52) U.S. Cl.
   CPC ...... *A61B 1/00066* (2013.01); *A61B 1/00071*
        (2013.01); *A61B 1/00142* (2013.01); *A61B
        1/00165* (2013.01); *A61B 1/018* (2013.01);
            *A61B 1/00121* (2013.01); *A61B 1/00195*
                       (2013.01); *A61B 1/07* (2013.01)

(56) References Cited

U.S. PATENT DOCUMENTS

| | | | |
|---|---|---|---|
| 6,419,628 B1 | 7/2002 | Rudischhauser et al. | |
| 6,527,707 B1 * | 3/2003 | Frische | A61B 1/012 600/153 |
| 7,645,231 B2 * | 1/2010 | Akiba | A61B 1/00068 600/154 |
| 8,246,536 B2 * | 8/2012 | Ochi | A61B 1/00071 600/123 |
| 8,317,684 B2 * | 11/2012 | Matsuo | A61B 1/0011 600/140 |
| 8,911,355 B2 * | 12/2014 | Takeuchi | F16L 47/32 600/104 |
| 9,782,058 B2 * | 10/2017 | Ogawa | A61B 8/12 |
| 10,716,461 B2 * | 7/2020 | Jenkins | A61B 1/00128 |
| 2005/0182353 A1 | 8/2005 | Schmidberger et al. | |
| 2006/0129030 A1 | 6/2006 | Dehmel | |
| 2007/0088200 A1 | 4/2007 | Dahmen et al. | |
| 2008/0097160 A1 | 4/2008 | Salvermoser et al. | |
| 2011/0040148 A1 | 2/2011 | Dahmen et al. | |
| 2017/0010458 A1 * | 1/2017 | Nishijima | A61B 1/00071 |
| 2017/0209021 A1 | 7/2017 | Salvermoser et al. | |

FOREIGN PATENT DOCUMENTS

| | | |
|---|---|---|
| DE | 102004059255 B3 | 5/2006 |
| DE | 102006030521 A1 | 1/2008 |
| EP | 1776918 A2 | 4/2007 |
| EP | 2283767 A1 | 2/2011 |
| JP | 2000-121962 A | 4/2000 |

OTHER PUBLICATIONS

Japanese Office Action dated Jan. 28, 2020 in Japanese Patent Application No. 2018-536862.

\* cited by examiner

PRIOR ART

SURGICAL INSTRUMENT AND METHOD FOR PRODUCING A SURGICAL INSTRUMENT

CROSS-REFERENCE TO RELATED APPLICATION

The present application is a continuation of PCT/EP2017/052556 filed on Feb. 6, 2017, which is based upon and claims the benefit to DE 10 2016 2019 05.8 filed on Feb. 9, 2016, the entire contents of each of which are incorporated herein by reference.

BACKGROUND

Field

The present disclosure relates to a surgical instrument and more particularly to a surgical instrument with an elongated shaft tube, which is adjoined by a main body, and with a connection body, wherein the connection body is coupled to a proximal end region of the shaft tube and wherein at least one working channel tube is arranged in an interior of the shaft tube, which working channel tube extends in a longitudinal direction of the shaft tube. The present disclosure further relates to a method for producing a surgical instrument.

Prior Art

In urology, urethroscopes are used as surgical instruments for endoscopic procedures in the renal pelvis. In order to enter into this region endoscopically, the urethroscope is advanced from outside through the urethra into the bladder and from there is inserted into the ureter (urinary duct). The shaft tube of a urethroscope frequently has a length of 400 mm; its diameter is about 3 to 4 mm. In order to lend the shaft tube the necessary stability with this extremely long and thin configuration, it is usually a metal tube. Urethroscopes as surgical instruments with a rigid or partially rigid shaft are known.

At least one observation device, a plurality of light guides for lighting the operation field and at least one, frequently two, working channels are present in an interior surrounded by the shaft tube. The working channels each extend in a working channel tube. Instruments, for example catheters, forceps, lithotripters or similar, are guided through the working channel tubes into the operation area. A urethroscope is known, for example, from DE 10 2004 059 255 B3.

After use in surgery, the urethroscopes are prepared, i.e., cleaned and disinfected. In the context of the disinfection, the surgical instruments are frequently treated in an autoclave. In order to prevent the cleaning and/or preparing liquid or the steam used for autoclaving from penetrating into the interior of the surgical instrument, the working channels on the proximal end of the urethroscope are sealed with respect to the main body of the urethroscope with the assistance of a seal assembly. The reliability of these seals, however, diminishes over time. Therefore, the seals must be checked at regular intervals and replaced if necessary.

FIG. 2 shows a schematically simplified longitudinal section view of the region of a proximal end region 16 of a working channel tube 18 of a urethroscope according to the prior art. The working channel tube 18 is sealed in its proximal end region 16 on its outer jacket surface with respect to an intermediate body 22 with the assistance of a first O-ring seal 20. This intermediate body 22 is sealed with a second O-ring seal 24 with respect to an inner jacket surface of the main body 6 (only a section of which is represented). The first and the second O-ring seal 22, 24 must be replaced or respectively checked at regular intervals in order to ensure a reliable seal of the working channel tube 18 with respect to the main body 6.

For this reason, conventional urethroscopes are designed in that the accessibility of the seal elements is ensured. However, this necessitates a not insignificant amount of constructive effort. In addition, the maintenance of the seal elements that must be carried out regularly is time-consuming and costly.

SUMMARY

An object is to provide a surgical instrument as well as a method for producing a surgical instrument, wherein the surgical instrument is simple to prepare, maintenance-friendly and constructively simple.

Such object can be solved by a surgical instrument with an elongated shaft tube, which is adjoined by a main body, and with a connection body, wherein the connection body is coupled to a proximal end region of the main body and wherein at least one working channel tube is arranged in an interior of the shaft tube, which working channel tube extends in a longitudinal direction of the shaft tube, wherein a proximal end region of the working channel tube is accommodated inside the connection body and is sealed with respect thereto.

The working channel can be sealed directly with respect to the connection body and not, as is conventional instruments, with respect to the main body. With these measures, preparing medium is prevented from entering the internal free or hollow spaces of the surgical instrument during the preparing process. Therefore, it is simple and reliable to prepare. Furthermore, the seal between the working channel tube and the shaft tube as well as between the working channel tube and the main body can advantageously be omitted, such as the sealing rings usually used there. The working channel tube is already sealed with respect to the connection body. Maintenance of the seals is also advantageously dispensed with.

The proximal end region of the working channel tube can be sealed with respect to the connection body by means of an adhesive connection.

With the provided adhesive connection, the problems that arise in this region with traditionally designed surgical instruments are eliminated. With conventional instruments, O-ring seals are used to seal the proximal end region of a working channel tube, which, however, require regular maintenance. Furthermore, conventional surgical instruments must be designed in that the seals are accessible. The proximal end region of the working channel tube can be continued into the connection body and in addition is connected inside it by means of an adhesive connection. As a result, a low-maintenance and constructively simple surgical instrument is provided that can be prepared very well.

According to another embodiment, the connection body can comprise at least one feed channel that communicates, such as aligns, with a working channel that is surrounded by the working channel tube, wherein the end region of the working channel tube is accommodated in the feed channel of the connection body and is sealed with respect to the connection body by means of an adhesive connection between an inner wall of the feed channel and a jacket surface of the working channel tube.

The direct connection of the working channel tube to the feed channels in the connection body, prevents free or hollow spaces that are present in the interior of the surgical instrument from being accessible for the cleaning medium. Such spaces are always difficult to clean. Such surgical instrument, however, is easy to prepare.

According to another embodiment, the working channel tube can be connected to the main body by means of a shaft-shaped seal shoulder.

The shaft-shaped seal shoulder allows a mechanically reliable coupling of the working channel tube. Such a mechanically loadable and reliable connection can be important in the case of a surgical instrument with a partially rigid, i.e., to a certain degree flexible, shaft. This is true when the surgical instrument is a urethroscope.

The shaft-shaped seal shoulder can be connected on its inner wall to a proximal end region of the working channel tube and on its outer jacket surface to a proximal end region of the main body.

The working channel tube is a component with low wall and material thickness. In the case of surgical instruments with a partially rigid shaft, such as, urethroscopes, the working channel tube is subjected to pressure and tensile loads during a bending motion of the shaft that cannot be disregarded. In order to provide the necessary mechanical stability of the connection between the working channel tube and the main body, it is provided according to another embodiment that the shaft-shaped seal shoulder comprises a jacket section and a connecting section, wherein the connecting section has a greater material thickness in a radial direction than the jacket section, and the jacket section is connected to the working channel tube by means of at least one linear through-weld connection that extends at least approximately in the longitudinal direction.

The linear through-weld connection can be a laser-welded connection.

With such laser welding, components with a low material thickness can be connected to each other reliably. The shaft-shaped seal shoulder provides a jacket section for the connection between the seal shoulder and the working channel tube. This jacket section can have the shape of a hollow cylinder with a low wall thickness. The connecting section can also have the shape of a hollow cylinder with, however, a significantly greater wall thickness and shorter length in comparison to the jacket section. This ensures that enough material is present in the connecting section of the shaft-shaped seal shoulder for a reliable connection to the main body, such as with a (laser) welding method. The jacket section is, however, slightly flexible and therefore follows the deformation of the working channel tube to a certain extent. The jacket section and the connecting section of the seal shoulder can be a single piece of material. In other words, the seal shoulder can be a turned workpiece made from a blank.

According to another embodiment, a hollow space adjacent to the seal shoulder can be provided in the connection body proximal to the seal shoulder between the main body and the connection body, wherein the proximal end region of the working channel tube is connected to the connection body with an adhesive connection and the hollow space is separated from the adhesive connection by a sealing means, such as, a sealing ring that is present between an outer jacket surface of the working channel tube and the connection body, wherein the adhesive connection can be provided by an adhesive that is hardened under the influence of heat.

When the adhesive is hardened under the influence of heat, the air present in the hollow space is also heated. This hollow space is a hollow space that is not accessible from the interior of the working channel. The sealing ring prevents a pressure load (from the expanding air) on the adhesive connection from resulting during this process. This could generate micro-channels in the not yet fully hardened adhesive mass, which could call into question the hermetic seal tightness of the adhesive connection.

According to another embodiment, at least one of the following connections can be a laser-welded connection:
the connection between the main body and the connection body,
the connection between the seal shoulder and the proximal end region of the main body,
the connection between the shaft tube and the main body.

The multiple linear laser-welded connections, which connect the shaft-shaped seal shoulder on its inner wall to an outer jacket surface of the proximal end region of the working channel tube, extend in the longitudinal direction of the working channel tube and can be arranged evenly distributed along its circumference. In this way, a reliable and mechanical connection between the working channel tube and the shaft-shaped seal shoulder can be created.

The shaft-shaped seal shoulder can accommodate pressure and/or tensile forces that act upon the working channel tube and conduct them into the main body or respectively the shaft tube. This is important for surgical instruments with a partially rigid, elongated shaft tube. The working channel tube is regularly not guided along a line that is neutral for the bending of the shaft tube so that it must accommodate pressure and/or tensile forces when the shaft tube is bent.

According to another embodiment, the shaft or respectively the shaft tube of the surgical instrument can be rigid or partially rigid. In other words, it is flexible to a specified degree. Furthermore, according to one embodiment, the surgical instrument is a urethroscope.

Furthermore, the connection between the working channel tube and the shaft-shaped seal shoulder can be surface-bonded. Such a surface-bonded connection is, for example, a weld connection, such as a laser-welded connection.

Such object can be further solved by a method for producing a surgical instrument with an elongated shaft tube, which is adjoined by a main body, and with a connection body, wherein the connection body is coupled to a proximal end region of the main body and wherein at least one working channel tube is arranged in an interior of the shaft tube, which working channel tube extends in a longitudinal direction of the shaft tube, wherein a proximal end region of the working channel tube is accommodated inside the connection body and is sealed with respect thereto.

The same or similar advantages apply to the method for producing the surgical instrument that were mentioned above with reference to the surgical instrument itself, and they will therefore not be repeated.

According to an embodiment, the proximal end region of the working channel tube can be sealed with respect to the main body by means of an adhesive connection.

In a method according to another embodiment, the working channel tube can be connected to a shaft-shaped seal shoulder and the shaft-shaped seal shoulder can be connected to the connection body.

Furthermore, the shaft-shaped seal shoulder can comprise a jacket section and a connecting section, wherein the connecting section has a greater material thickness in a radial direction than the jacket section, and the jacket section is connected to the working channel tube with at least one linear through-welding connection that extends at least approximately in the longitudinal direction.

A proximal end region of the shaft tube can regularly include the proximal end of the shaft tube. The proximal end region extends, starting from this proximal end of the shaft tube, in the distal direction. For example, such a proximal end region is a few centimeters long and in relation to the overall length of the shaft tube takes up a small percentage of its length, for example less than 10%. The same is true for the end region of the working channel tube.

According to another embodiment, the linear through-weld connection can be produced with a laser welding method.

With a laser welding method, components with a low wall or material thickness can be connected to each other reliably. For this reason, such a method can be suitable for producing the weld connection between the working channel tube and the jacket section of the shaft-shaped seal shoulder.

Between the proximal end region, in which the working channel tube is connected by means of the adhesive connection to the connection body, and the hollow space, a sealing means, such as a sealing ring, can be provided between an outer jacket surface of the working channel tube and the connection body so that the adhesive connection and the hollow space are separated from each other.

The sealing ring can be, for example, an O-ring, which is arranged between the outer jacket surface of the working channel tube and the main body.

According to another embodiment, a plastic that can be hardened under the influence of heat can be used for the adhesive connection. Furthermore, the adhesive can be hardened by the influence of heat in order to produce the adhesive connection. In the process, for example, the entire surgical instrument can be heated to the temperature necessary for hardening the adhesive.

Furthermore, at least one of the following connections can be produced as a laser-welded connection:
the connection between the proximal main body and the connection body,
the connection between the seal shoulder and the proximal end region of the main body,
the connection between the shaft tube and the main body.

The method for producing a surgical instrument can be a method for producing a urethroscope.

BRIEF DESCRIPTION OF THE DRAWINGS

Further features will become apparent from the description of the embodiments together with the claims and the attached drawings. Embodiments can fulfill individual features or a combination of several features.

The embodiments are described below, without restricting the general idea, using exemplary embodiments with reference to the drawings, wherein express reference is made to the drawings with regard to all details that are not explained in greater detail in the text. In the figures.

In the drawings, in each case the same or similar elements and/or parts are provided with the same reference numbers, so that in each case a repeated introduction is omitted.

DETAILED DESCRIPTION

Figure 1:
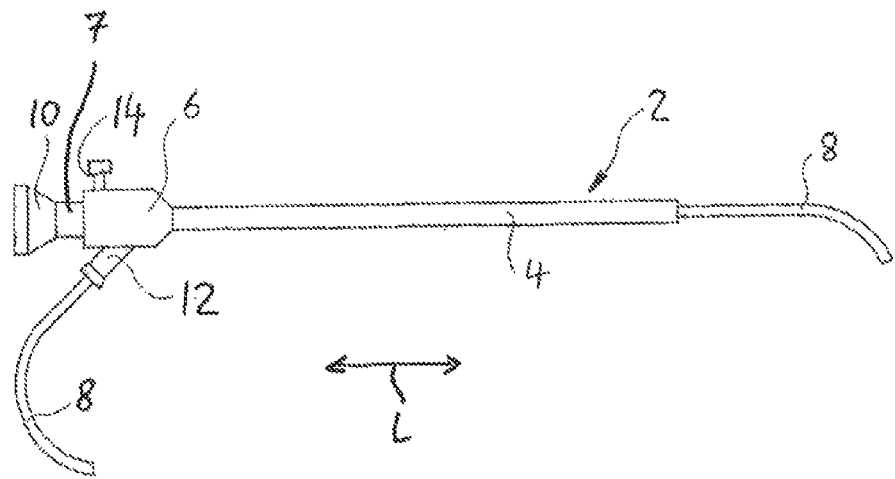
FIG. 1 illustrates a schematic side view of a urethroscope as an exemplary surgical instrument.

FIG. 1 shows a schematically simplified side view of a surgical instrument 2. As an example, a urethroscope is represented. The surgical instrument 2 comprises an elongated shaft tube 4 that extends in a longitudinal direction L. A proximal end region of the shaft tube 4 is coupled to a main body 6. In the proximal direction, a connection body 7 is adjoined by the main body 6. In an interior surrounded by the shaft tube 4, a working channel tube 18 is arranged (not visible in FIG. 1) that extends in the longitudinal direction L. A treatment instrument 8, for example a catheter, forceps or a lithotripter, is guided through the interior of the working channel tube 18, i.e., the working channel, into an operation area. Furthermore, optical fibers for lighting the operation area as well as a corresponding optical system extend in the shaft tube 4 in order to view the operation area through an eyepiece 10. The treatment instrument 8 is fed to the surgical instrument 2 through an insertion part 12 adjoined by the connection body 7. The optical fibers provided for lighting the operation area are supplied via the light guide connection 14 on the main body 6.

Figure 2:
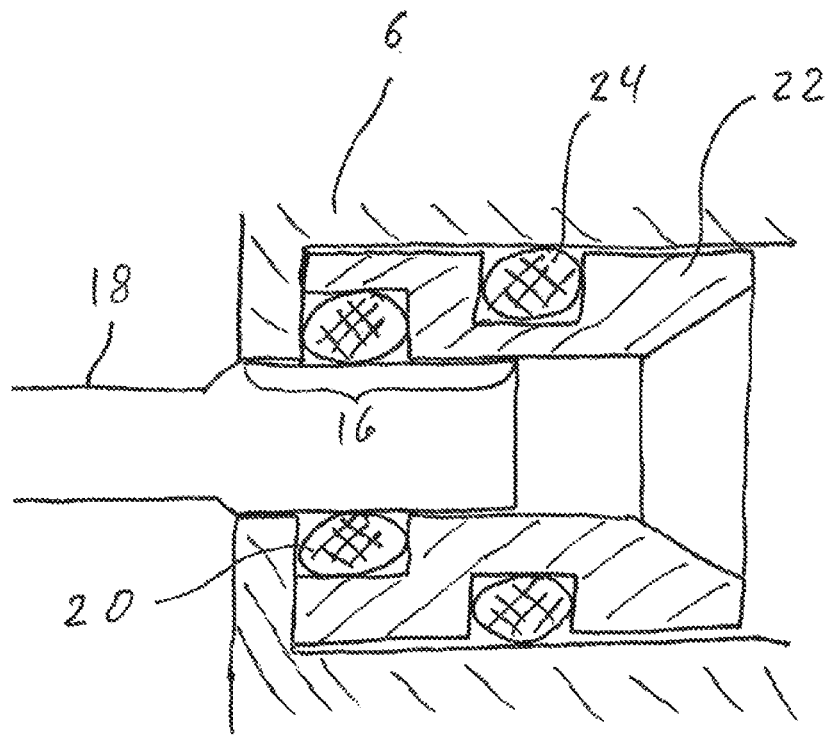
FIG. 2 illustrates a schematically simplified longitudinal section view in the region of a proximal end region of a working channel tube of a urethroscope according to the prior art.

In contrast to the prior art, such as that illustrated in FIG. 2, the surgical instrument 2 is configured in that the working channel tube 18 is accommodated directly in the connection body 7 and is sealed with respect thereto. The surgical instrument 2 is described in more detail below.

Figure 3:
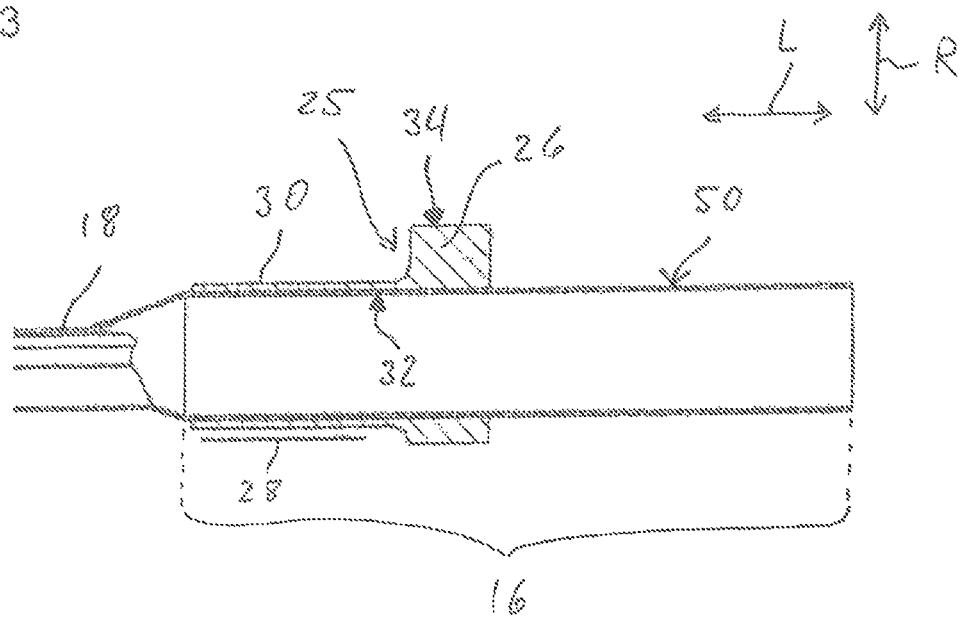
FIG. 3 illustrates a schematically simplified longitudinal section view through a proximal end region of a working channel tube that is provided with a shaft-shaped seal shoulder.

In the schematically simplified longitudinal section view from FIG. 3, it is shown that a proximal end region 16 of the working channel tube 18 is connected to a shaft-shaped seal shoulder 25. The shaft-shaped seal shoulder 25 comprises a jacket section 30 and a connecting section 26. The jacket section 30 is implemented with a low material thickness and therefore has a certain flexibility in a radial direction R. The material thickness in this radial direction R is considerably lower in the jacket section 30 than in the connecting section 26. In the longitudinal direction L, the jacket section 30 is longer than the connecting section 26. The jacket section 30 and connecting section 26 are parts of the shaft-shaped seal shoulder 25 can that be produced from a single piece of material/integrally.

The connection between the seal shoulder 25 and the proximal end region 16 of the working channel tube 18 occurs, for example, with the assistance of a laser-welded connection, such as with the assistance of multiple laser-welded connections. For example, laser weld lines 28 oriented in the longitudinal direction L are set, one of which is exemplarily and schematically indicated in FIG. 3. The laser weld lines 28 are arranged, such as being evenly distributed, along the circumference of the jacket section 30 of the seal shoulder 25, i.e., they can have the same distances to each other in the circumferential direction. The laser weld connections can be through-weld connections. The shaft-shaped jacket section 30 of the seal shoulder 25 that is made with a lower material thickness is fixed to the outer jacket surface 50 of the working channel tube 18 in its proximal end region 16.

In a laser weld connection, the energy brought in can be dosed so well that components with a low material thickness can be connected to each other reliably without a perforation of the components occurring. This is not or only limitedly possible with conventional methods for producing weld connections.

The working channel tube 18 with the seal shoulder 25 fastened thereto is subsequently brought into the main body 6 of the surgical instrument 2.

Figure 4:
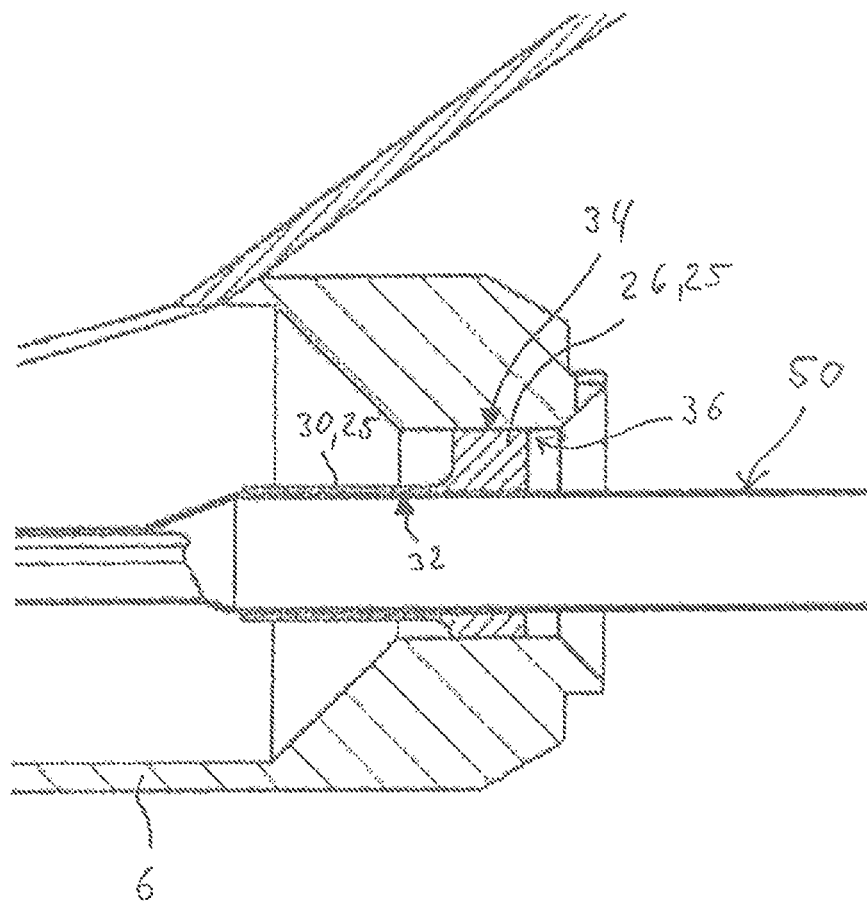
FIG. 4 illustrates a schematically simplified longitudinal section view of such a working channel tube with the seal shoulder placed onto it, said working channel tube being introduced in a main body.

In FIG. 4, a schematically simplified longitudinal section view of the working channel tube 18 with the seal shoulder 25 placed onto it is shown, wherein the working channel tube 18 is introduced into the main body 6.

While the jacket section 30 of the seal shoulder 25 is connected on its inner wall 32 to the proximal end region 16, i.e., the outer jacket surface 50 of the working channel tube 18, the connecting section 26 of the seal shoulder 25 is connected on its outer jacket surface 34 to a proximal end region 16 of the main body 6. In this way, a mechanical connection between the main body 6 and the working channel tube 18 is produced.

The connection between the main body 6 and the working channel tube 18 via the seal shoulder 25 occurs, for example, in that a weld seam produced with the assistance of a laser is set in the neck 36 between the seal shoulder 25 and an inner jacket surface of the proximal end of the shaft tube 4. The weld seam set in the neck 36 can be implemented fully or discontinuously.

Subsequently, the connection body 7 is placed onto the main body 6, wherein the proximal end region 16 of the working channel tube 18 is accommodated in the connection body 7 and is sealed with respect thereto with the assistance of an adhesive connection 38 (see FIG. 5).

Figure 5:
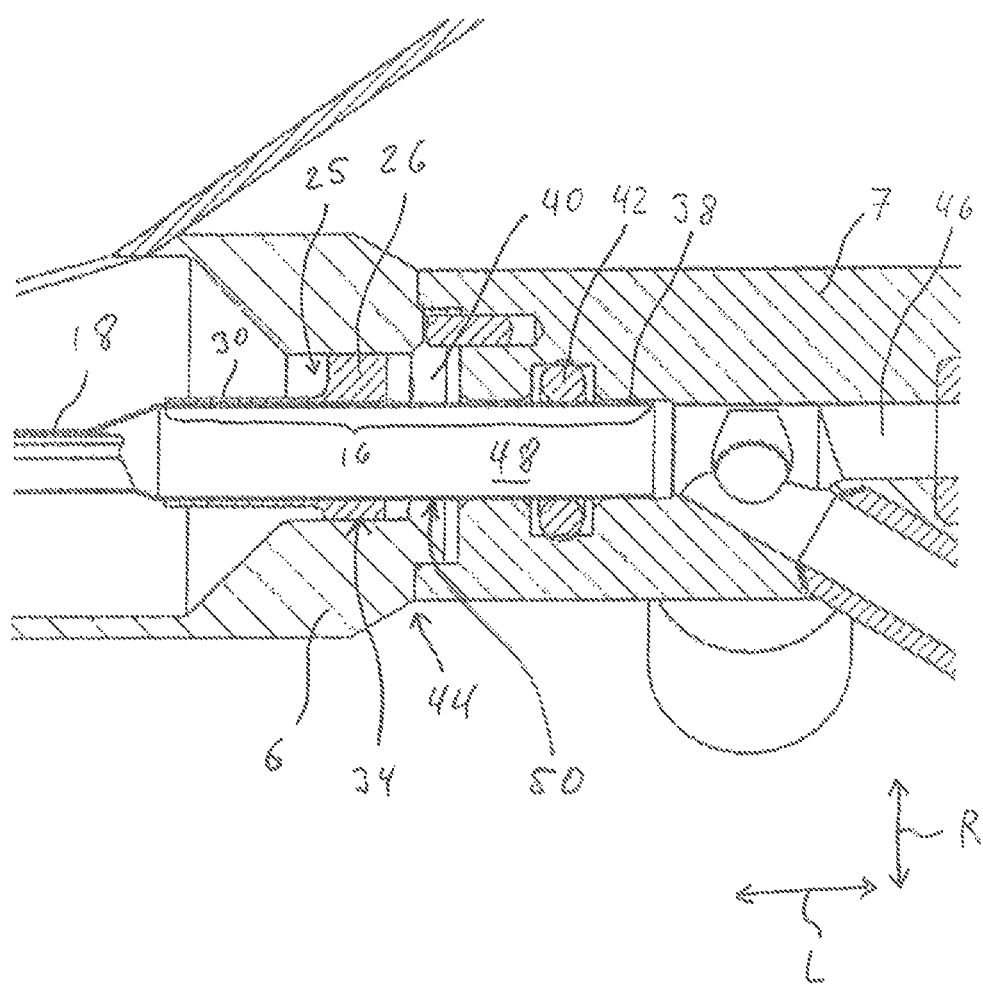
FIG. 5 illustrates a detailed representation of a completely mounted urethroscope as an exemplary surgical instrument in a schematically simplified longitudinal section view in the region of the proximal end region of the working channel tube.

FIG. 5 shows a detailed representation of a completely mounted surgical instrument 2 in a schematically simplified longitudinal section view. The adhesive connection 38 is implemented circumferentially, i.e., extending along the full circumference of the working channel tube 18. The adhesive connection lies in the proximal end region 16. With the adhesive connection, a fluid-tight connection between the connection body 7 and the working channel tube 18 is produced.

An adhesive can be used that hardens through the influence of heat. In order to harden the adhesive for producing the adhesive connection 38, the complete surgical instrument 2, for example, is heated.

Proximal to the seal shoulder 25, a hollow space 40 adjacent to the seal shoulder 25 is present in the connection body 7 between the main body 6 and the connection body 7. If the air present in this hollow space 40 heats up during the hardening of the adhesive connection 38, the overpressure arising in the hollow space 40 may not interfere with the adhesive connection 38, which is possibly not yet hardened.

Before the adhesive connection 38 is fully hardened, no overpressure should act upon it. Therefore, a sealing means 42 is provided between the hollow space 40 and the adhesive connection 38. The sealing means 42 is, for example, a sealing ring (O-ring). This is present between an outer jacket surface 50 of the working channel tube 18 in its proximal end region 16 and the connection body 7. This ensures that the adhesive connection 38 and the hollow space 40 are fluidly separated from each other.

The connection body 7 is connected to the main body 6 in that a laser-welded connection can be produced circumferentially on the contact location 44 between these two components. This connection can be hermetically sealed.

Furthermore, the connection body 7 can comprise at least one feed channel 46 that communicates, such as aligning, with the working channel 48 that is surrounded by the working channel tube 18. A treatment instrument 8 (cf. FIG. 1) is inserted into the working channel 48 through the feed channel 46 and is pushed through the surgical instrument 2 into a treatment space. The proximal end region 16 of the working channel tube 18 is accommodated in the feed channel 46 of the connection body 7 and is sealed with respect to the connection body 7 by means of the adhesive connection 38 between an inner wall of the feed channel 46 and an outer jacket surface 50 of the working channel tube 18.

In a method for producing a surgical instrument 2, such as a urethroscope, the steps represented in FIGS. 3 to 5 are implemented sequentially. First, the seal shoulder 25 is arranged in the proximal end region 16 of the working channel tube 18 and is fixed, such as by means of laser weld connections. Subsequently, the working channel tube 18 is introduced in the main body 6 and the seal shoulder 25 is connected on its outer jacket surface 34 to the inner jacket surface of the main body 6 on its proximal end region 16. For this, a laser-welded connection can be set in the neck 36. Finally, the connection body 7 is placed onto the main body 6, wherein adhesive is applied to the end of the proximal end region 16 in order to produce the adhesive connection 38. The connection body 7 is connected to the main body 6, once again, such as by forming a laser-welded connection. For this, a circumferential laser-welded seam is set, for example on the contact location 44. In order to connect the working channel tube 18 to the connection body 7, the surgical instrument 2 is heated so that the applied adhesive hardens and the adhesive connection 38 is provided.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE SIGN LIST

2 Surgical instrument
4 Shaft tube
6 Main body
7 Connection body
8 Treatment instrument
10 Eyepiece
12 Insertion part
14 Light guide connection
16 Proximal end region
18 Working channel tube
20 First O-ring seal
22 Intermediate body
24 Second O-ring seal
25 Seal shoulder
26 Connecting section
28 Laser weld line
30 Jacket section
32 Inner wall
34 Outer jacket surface
36 Neck
38 Adhesive connection 40 Hollow space
42 Sealing means
44 Contact location
46 Feed channel
48 Working channel
50 Outer Jacket Surface
L Longitudinal direction
R Radial direction

The invention claimed is:

1. A surgical instrument comprising:
a main body;
an elongated shaft tube connected to the main body, the shaft tube having at least one working channel tube arranged in an interior of the shaft tube, the at least one working channel tube extending in a longitudinal direction of the shaft tube; and
a connection body coupled to a proximal end region of the main body;
wherein a proximal end region of the at least one working channel tube is accommodated inside the connection body and is sealed with respect to the connection body;
the at least one working channel tube is connected to the main body with a shaft-shaped seal shoulder; and
the shaft-shaped seal shoulder comprises a jacket section and a connecting section, the connecting section having a greater material thickness in a radial direction than the jacket section, and the jacket section is connected to the at least one working channel tube by at least one linear through-weld connection that substantially extends in the longitudinal direction.

2. The surgical instrument according to claim 1, further comprising an adhesive for sealing the proximal end region of the at least one working channel tube with respect to the connection body.

3. The surgical instrument according to claim 1, wherein the connection body comprises at least one feed channel that communicates with a working channel that is surrounded by the at least one working channel tube, wherein the proximal end region of the at least one working channel tube is accommodated in the at least one feed channel of the connection body and is sealed with respect to the connection body by an adhesive disposed between an inner wall of the at least one feed channel and an outer jacket surface of the at least one working channel tube.

4. The surgical instrument according to claim 3, wherein the at least one feed channel aligns with the working channel.

5. The surgical instrument according to claim 4, wherein the shaft-shaped seal shoulder is connected on its inner wall to the proximal end region of the at least one working channel tube and on its outer jacket surface to a proximal end region of the main body.

6. The surgical instrument according to claim 1, wherein the linear through-weld connection is a laser-welded connection.

7. The surgical instrument according to claim 1, wherein a hollow space is provided adjacent to the shaft-shaped seal shoulder, the hollow space being proximal to the shaft-shaped seal shoulder and at a transition between the main body and the connection body, wherein the proximal end region of the at least one working channel tube is connected to the connection body with an adhesive and the hollow space is separated from the adhesive by a seal disposed between an outer jacket surface of the working channel tube and the connection body, the adhesive being of a type that is hardened under the influence of heat.

8. The surgical instrument according to claim 7, wherein the seal is a sealing ring.

* * * * *